United States Patent [19]
Chandraratna et al.

[11] Patent Number: 5,231,113
[45] Date of Patent: Jul. 27, 1993

[54] TETRALIN ESTERS OF PHENOLS OR BENZOIC ACIDS HAVING RETINOID LIKE ACTIVITY

[75] Inventors: Roshantha A. S. Chandraratna, El Toro; Robert J. Weinkam, Laguna Hills, both of Calif.

[73] Assignee: Allergan, Inc., Irvine, Calif.

[21] Appl. No.: 894,122

[22] Filed: Jun. 4, 1992

Related U.S. Application Data

[60] Division of Ser. No. 558,737, Jul. 27, 1990, Pat. No. 5,130,335, which is a continuation of Ser. No. 179,700, Apr. 11, 1988, abandoned.

[51] Int. Cl.$^5$ .................. A61K 31/235; C07C 69/75; C07C 69/82; C07C 327/26
[52] U.S. Cl. .................. 514/510; 514/513; 514/533; 514/538; 514/541; 514/544; 558/254; 558/255; 560/41; 560/44; 560/51; 560/60; 560/61; 560/81; 560/85
[58] Field of Search .............. 514/510, 513, 533, 538, 514/541, 544; 558/254, 255; 560/41, 44, 51, 60, 61, 81, 85

[56] References Cited

U.S. PATENT DOCUMENTS

| | | | |
|---|---|---|---|
| 4,096,341 | 6/1978 | Frazer | 560/85 |
| 4,391,731 | 7/1983 | Boller et al. | 252/299.62 |
| 4,695,649 | 9/1987 | Magami et al. | 560/86 |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |

OTHER PUBLICATIONS

Sporn et al. in *J. Amer. Acad. Derm.* 15:756–764 (1986).
Shudo et al., *Chem. Phar. Bull.*, 33:404–407 (1985).

*Primary Examiner*—José G. Dees
*Assistant Examiner*—Vera C. Clarke
*Attorney, Agent, or Firm*—Gabor L. Szekeres; Martin A. Voet; Robert J. Baran

[57] ABSTRACT

Retinoid-like activity is exhibited by compounds of the formula

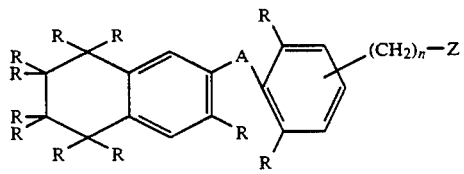

where the R groups are independently hydrogen, or lower alkyl; A is —C(O)O—, —OC(O)—, —C(O)S—, or —SC(O)—; n is 0-5; and Z is H, —COB where B is —OH or a pharmaceutically acceptable salt, or B is —OR$_1$ where R$_1$ is an ester-forming group, or B is —N(R)$_2$ where R is hydrogen or lower alkyl, or Z is —OE where E is hydrogen or an ether-forming group or —COR$_2$ where R$_2$ is hydrogen, lower alkyl, phenyl or lower alkyl phenyl, or Z is —CHO or an acetal derivative thereof, or Z is —COR$_3$ where R$_3$ is —(CH$_2$)$_m$CH$_3$ where m is 0-4 and the sum of n and m does not exceed 4.

11 Claims, No Drawings

TETRALIN ESTERS OF PHENOLS OR BENZOIC ACIDS HAVING RETINOID LIKE ACTIVITY

CROSS-REFERENCE TO RELATED APPLICATIONS

This application is a divisional of application Ser. No. 07/558,737 filed on Jul. 27, 1990 issued as U.S. Pat. No. 5,130,335, which is a continuation of application Ser. No. 07/179,700 filed on Apr. 11, 1988, now abandoned.

BACKGROUND

This invention relates to novel compounds having retinoid-like activity. More specifically, the invention relates to compounds comprising a tetralin ester of phenolic acids and terephthallic acids. The acid function of the phenyl containing moiety may also be converted to an alcohol, aldehyde or ketone or derivatives thereof, or that group may be alkyl or H.

RELATED ART

Compounds of similar nature wherein A is —C(O)—N(H)— are discussed in an article in the Am. Academy of Dermatology, Sporn, M. B., et al., V. 15, No. 4, p 756 (1986); a communication by Kagechika, H., et al, in Chem. Pharm. Bull., 32, (10) 4209 (1984) and another communication by Shudo, K, et al., in Chem. Pharm. Bull., 33 (1) 404–407 (1985).

SUMMARY OF THE INVENTION

This invention covers compounds of formula I

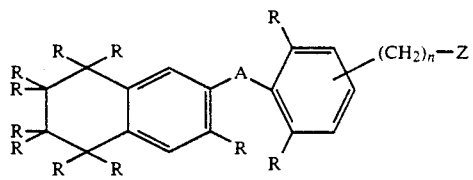

where the R groups are independently hydrogen, or lower alkyl; A is —C(O)O—, —OC(O)—, —C(O)S—, or —SC(O)—; n is 0–5; and Z is H, —COB where B is —OH or a pharmaceutically acceptable salt, or B is —OR$_1$ where R$_1$ is an ester-forming group, or B is —N(R)$_2$ where R is hydrogen or lower alkyl, or Z is —OE where E is hydrogen or an ether-forming group or —COR$_2$ where R$_2$ is hydrogen, lower alkyl, phenyl or lower alkyl phenyl, or Z is —CHO or an acetal derivative thereof, or Z is —COR$_3$ where R$_3$ is —(CH$_2$)$_m$CH$_3$ where m is 0–4 and the sum of n and m does not exceed 4.

In a second aspect, this invention relates to the use of the compounds of formula I for treating dermatoses such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing and in treating dry eye syndrome and in treating or reversing the effects of sum induced skin aging and damage.

This invention also relates to a pharmaceutical formulation comprising a compound of formula I in admixture with a pharmaceutically acceptable excipient, particularly a composition having anti-psoriatic activity.

In another aspect, this invention relates to the process for making a compound of formula I which process comprises reacting a compound where the X or Y of formula II or III is an acid or acid derivative which can form an ester with the corresponding formula II or III where X or Y is an —OH or —SH group, preferably in the presence of an ester-forming catalyst.

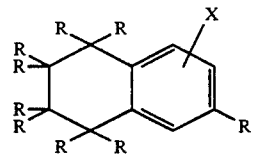

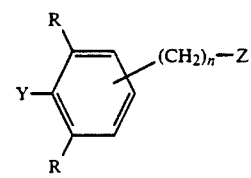

where R, n and Z are the same as defined above.

To synthesize compounds where n is 1 or greater and the corresponding formula III form is not commercially available, the acid of formula III where Z is COOH can be homologated to insert the desired number of methylene groups. This homologation product, the acid, can then be reduced to give the corresponding aldehyde or alcohol. Such compound can then be coupled with the corresponding formula II compound, the Z functional group being protected as necessary. Acids of formula I may be converted to their salts by treating them with the appropriate base under mild conditions. An acid of formula I can also be converted to an ester.

GENERAL EMBODIMENTS

Definitions

The term "ester" as used here refers to and covers any compound falling within the definition of that term as classically used in organic chemistry. Where Z is —COOH, this term covers the products derived from treatment of this function with alcohols. Examples are the C$_1$ to C$_6$ alkyl esters (lower alkyl) or C$_1$ to C$_6$ lower alkyl phenyl esters. Where the ester is derived from compounds where Z is —OH, this term covers compounds of the formula OC(O)R' where R' is any substituted or unsubstituted aliphatic, aromatic or aliphatic-aromatic group, particularly those of 7 to 10 carbons.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1–6 carbon atoms. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono-and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono-and di-substituted amides derived from the phenyl or lower alkylphenyl amines. Unsubstituted amides are also preferred.

Acetals and ketals includes the radicals of the formula —CK where K is (—OR')₂. Here, R' is lower alkyl. Also, K may be —OR₁O— where R₁ is lower alkyl of 2-5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di-and trialky amines or ethanol amines. Salts may also be formed with caffeine, tromethamine and similar molecules. Where there is a nitrogen sufficeintly basic as to be capable of forming acid addition salts, such may be formed with any inorganic or organic acids or alkylating agent such a methyl iodide. Preferred acid addition salts are those formed with inorganic acids such as hydrochloric acid, sulfuric acid or phosphoric acid. Any of a number of simple organic acids having one, two or three carboxyl groups may be used for making acid addition salts.

Herein, the following numbering system is used for the instant compounds.

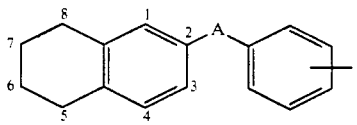

The preferred compounds of this invention are:
ethyl 4-(5,5,8,8-tetramethyl-5,6,7,8-tetrahydro-2-naphthoyloxy)benzoate
benzyl 4-(5,5,8,8-tetramethyl-5,6,7,8-tetrahydro-2-naphthoyloxy)benzoate,
pentadeuteroethyl 4-(5,5,8,8-tetramethyl-5,6,7,8-tetrahydro-2-naphthoyloxy)benzoate,
n-hexyl 4-(5,5,8,8-tetramethyl-5,6,7,8-tetrahydro-2-naphthoyloxy)benzoate,
n-tetradecyl 4-(5,5,8,8-tetramethyl-5,6,7,8-tetrahydro-2-naphthoyloxy)benzoate,
ethyl 4-(5,5,8,8-tetramethyl-5,6,7,8-tetrahydro-2-naphthoyloxy)-3-methylbenzoate,
4-(5,5,8,8-tetramethyl-5,6,7,8-tetrahydro-2-naphthoyloxy)benzamide,
4-methoxymethyl)phenyl)-5,5,8,8-tetramethyl-5,6,7,8-tetrahydro-2-naphthoate,
4-tert-butyldimethylsiloxymethy)lphenyl)-5,5,8,8-tetramethyl-5,6,7,8-tetrahydro-2-naphthoate,
4-formylphenyl)-5,5,8,8-tetramethyl-5,6,7,8-tetrahydro-2-naphthoate,
4-dimethoxymethylphenyl)-5,5,8,8-tetramethyl-5,6,7,8-tetrahydro-2-naphthoate,
ethyl 4-(3,5,5,8,8-pentamethyl-5,6,7,8-tetrahydro-2-naphthoyloxy)benzoate,
benzyl 4-(3,5,5,8,8-pentamethyl-5,6,7,8-tetrahydro-2-naphthoyloxy)benzoate,
4-methoxymethylphenyl-3,5,5,8,8-pentamethyl-5,6,7,8-tetrahydro-2-naphthoate,
4-(3,5,5,8,8-pentamethyl-5,6,7,8-tetrahydro-2-naphthoyloxy)benzoic acid,
ethyl 4-(5,5-dimethyl-5,6,7,8-tetrahydro-2-naphthoyloxy)benzoate,
benzyl 4-(5,5-dimethyl-5,6,7,8-tetrahydro-2-naphthoyloxy)benzoate,
4-(5,5-dimethyl-5,6,7,8-tetrahydro-2-naphthoyloxy)-benzoic acid,
benzyl (5,5,8,8-tetramethyl-5,6,7,8-tetrahydro-2-naphthyl)terephthallate,
ethyl (5,5,8,8-tetramethyl-5,6,7,8-tetrahydro-2-naphthyl)terephthallate, and
(5,5,8,8-tetramethyl-5,6,7,8-tetrahydro-2-naphthyl)hydrogenterephthallate.

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be useful.

Any common topical formulation such as a solution, suspension, gel, ointment, or salve and the like may be used. Preparation of such topical formulations are well described in the art of pharmaceutical formulations as exemplified, for example, in *Remington's Pharmaceutical Science*, Edition 17, Mack Publishing Company, Easton, Pa. For topical application, these compounds could also be administered as a powder or spray, particularly in aerosol form.

Other medicaments can be added to such topical formulation for such secondary purposes as treating skin dryness, providing protection against light; other medications for treating dermatoses, preventing infection, reducing irritation, inflammation and the like.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or for intramuscular injection.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a topical formulation containing between 0.01 and 0.5 milligrams per milliliter of formulation will constitute a therapeutically effective concentration. If administered systemically, an amount between 0.01 and 2 mg per kg body weight per day will effect a therapeutic or prophylatic result in most instances.

The retinoic acid-like activity of these compounds was confirmed through the classic measure of retinoic acid activity involving the effect of retinoic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.:* 1662–1670, 1975.

Specific Embodiments

The compound of this invention can be made by a number of different synthetic chemical pathways. To illustrate this invention, there is here outlined a series of steps which have been proven to provide the compounds of formula I when such synthesis is followed in fact and in spirit. The synthetic chemist will readily appreciate that the conditions set out here are specific embodiments which can be generalized to any and all of the compounds represented by formula I.

Compounds of formula I where A is —C(O)O— are prepared as follows:

Reaction Scheme I

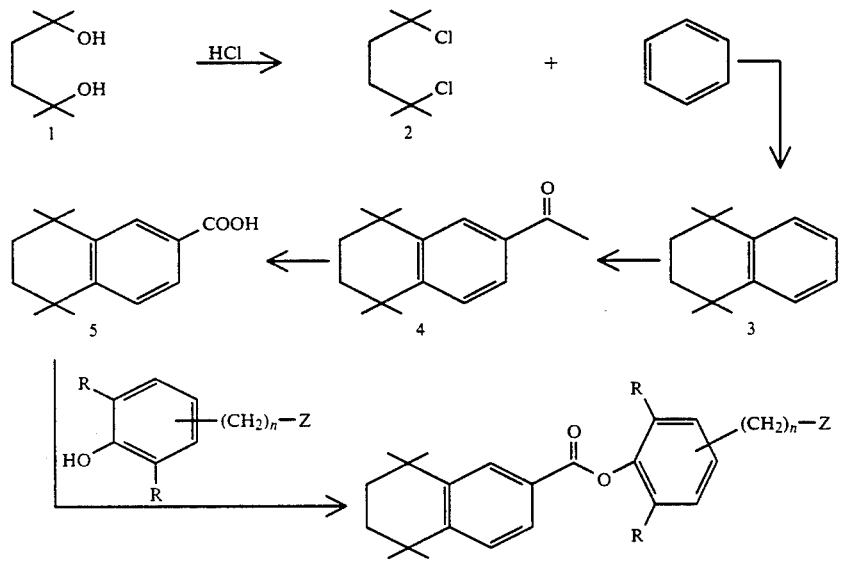

The case where position 2 on the tetrahydronaphthalene ring is alkyl (methyl) are made as follows.

Reaction Scheme IA

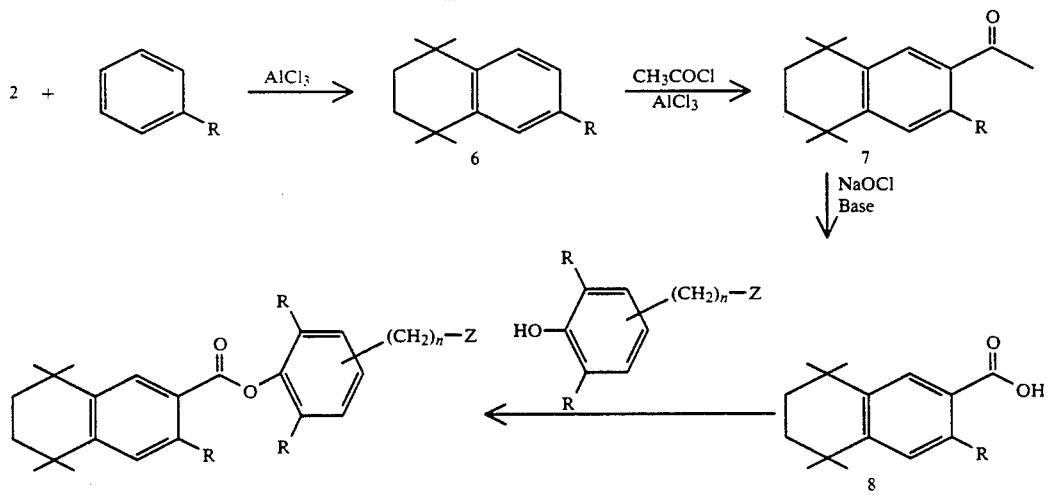

This reaction flow diagram illustrates specific compounds, but these illustrations can be generalized to all compounds disclosed herein including those where A is C(O)S or SC(O), by varying the starting materials or selecting the appropriate intermediate.

Compounds of formula I where A is —C(O)O—, and only the 5 or 8 positions on the tetrahydronaphthalene are methyl (alkyl) are prepared as per Reaction Scheme II.

2 by treating the dihydroxy compound with hydrogen chloride gas. The reaction is effected at room temperature or thereabout by bubbling hydrogen chloride gas through an aqueous hydrochloric acid suspension of the dihydroxy compound until a saturated solution is obtained. The dichloride precipitates from the solution

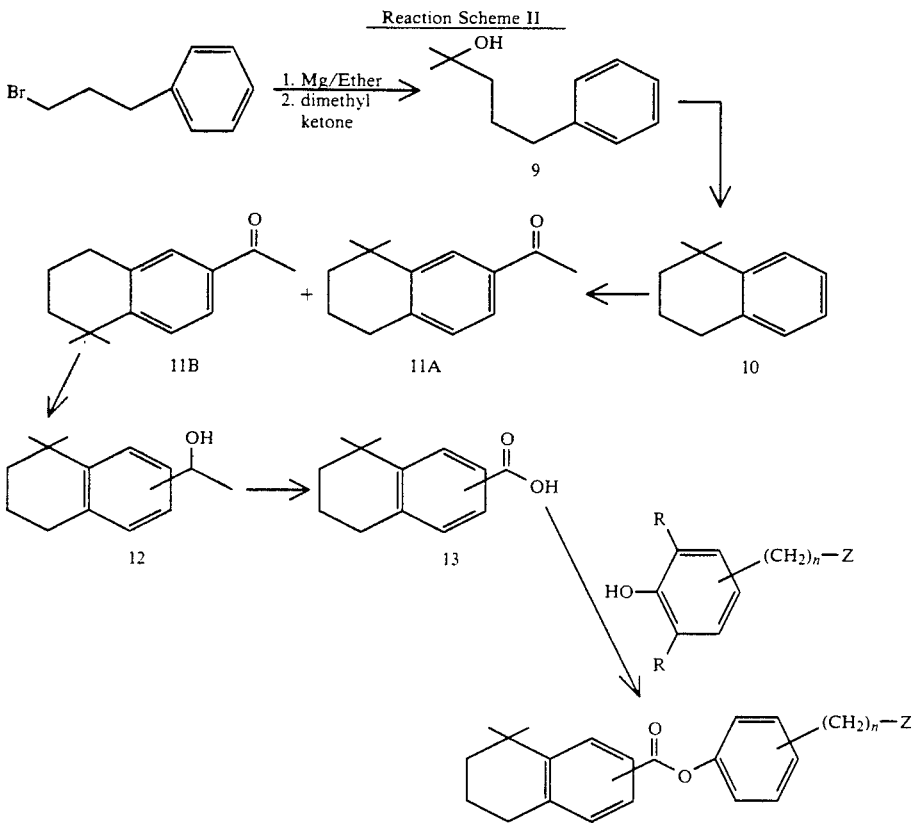

Compounds of formula I where A is —OC(O)— are prepared as per Reaction Scheme III.

during the process of saturation with hydrogen chloride gas. The crystalline precipitate is collected and repeat-

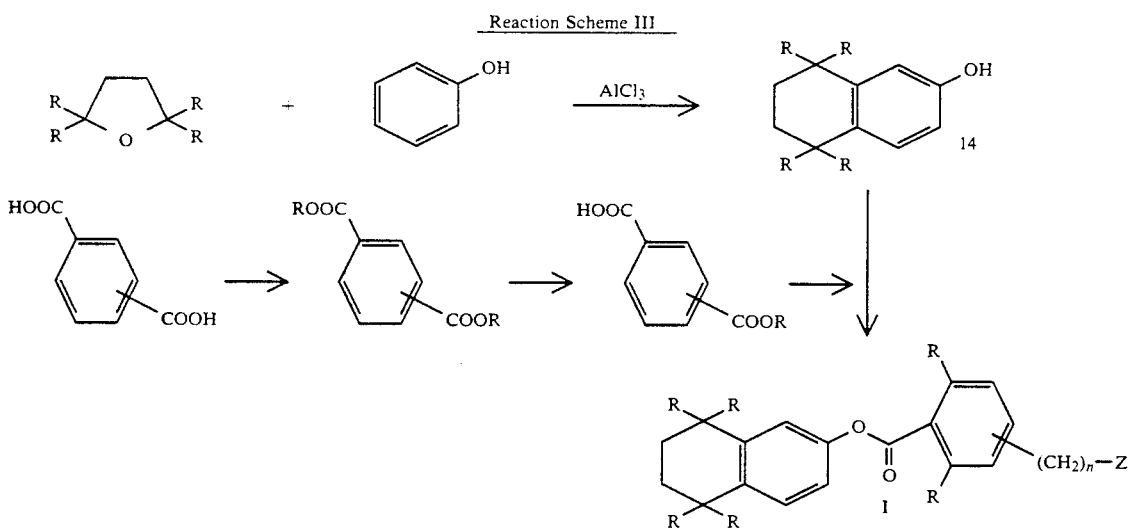

A general description for making the compounds recited in the foregoing schemes follows.

The 2,5-dihydroxy-2,5-dimethylhexane of formula 1 is converted to its corresponding dichloride of formula edly washed with water and then dried, for example, under vacuum.

Compound 3, the tetramethyltetrahydronaphthalene, and compound 6, (i.e. pentamethyltetrahydronaphthalene, in Reaction Scheme IA, are prepared by reacting the 2,5-dichloro-2,5-dimethylhexane compound with benzene and toluene, respectively under Friedel-Crafts conditions. For example, the 2,5-dichloro-material is dissolved in benzene which has been cooled to between about $-10°$ and $10°$ C. Approximately a 50% molar excess of anhydrous aluminum chloride relative to the 2,5-dichloro-material is added. After addition of the anhydrous aluminum chloride, the mixture is stirred at between about $10°$ and $50°$ C., preferably at room temperature, for between 1 and 6 hours, preferably 3 hours. The solution is then refluxed for about 30 minutes to 2 hours, but preferably approximately 1 hour. The resulting solution is acidified and the product recovered by extraction and other means such as fractional distillation.

The ketones of formula 4 or 7 in Scheme IA are obtained by treating the corresponding tetrahydronaphthalene with acetyl chloride in the presence of aluminum chloride. A suspension of aluminum chloride in a polar inert solvent is prepared under an inert atmosphere and at reduced temperature, i.e., $-10°$ to $10°$ C. The inert atmosphere may be argon or nitrogen, preferably argon. The reaction is conveniently carried out in a solvent such as methylene chloride. To the aluminum chloride suspension is added the tetrahydronaphthalene and acetyl chloride via a dropping funnel or similar device. About a 5% molar excess of acetyl chloride and 10% molar excess of aluminum chloride, relative to the tetrahydronaphthalene material, is used. The reaction is effected with agitation (stirring) over 0.5–4 hours at a temperature between $10°$–$50°$ C. Preferably the reaction is effected in about 2 hours at room temperature. Then the reaction is quenched with water and/or ice, the product extracted and further purified by distillation or some other appropriate means.

The carboxylic acid function (formulas 5 and 8) made by oxidizing the ketone with some oxidant such as a hypohalite salt or acid dichromate oxidant. Preferably the oxidant will be a hypohalite salt and the reaction will be carried out in the presence of a dilute base with a water-miscible organic solvent such as an ether. For example aqueous sodium hypochlorite in a four-fold excess or more, is mixed with dilute base such as 2N NaOH in dioxane along with the acetyl-substituted tetrohydronaphthalene. This mixture is heated at between about room temperature and 100 degrees for 30 minutes to 4 hours, preferably about 2 hours. A pot temperature of 60–70 degrees will affect the oxidation in this time period. After discarding the organic layer, a reducing agent is added to remove any residual oxidant. The solution is then acidified with a strong acid such as sulfuric acid and the tetrahydronaphthoic acid removed by conventional means.

Treating this acid, or its analogues, with the appropriate phenol or thiophenol gives compounds of formula I. Most means for esterification or thioesterification will provide the desired compounds of formula I. In these cases, esterification was effected by treating the appropriate acid and phenol with 1,3-dicyclohexylcarbodiimide and 4-dimethylaminopyridine.

If the Z group is an alcohol, aldehyde or ketone, it can first be protected before being used in the foregoing coupling reaction. Alcohols may be protected as ethers or esters, and aldehydes and ketones as acetals or ketals by known methods such as those described in *McOmie*, Plenum Publishing Press, 1973 and *Protecting Groups*, Ed. Greene, John Wiley & Sons, 1981. These same procedures can be used to make ethers, acetals and ketals at some other point in the synthetic process.

As regards Reaction Scheme II, the starting material, 1-bromo-3-phenylpropane, is readily available from any fine chemical house. Conversion of the primary bromide to the tertiary alcohol, formula 9, is effected by a Grignard type reaction using magnesium, dry solvent such as dry diethyl ether and acetone. The magnesium is first introduced into a dry flask under an inert atmosphere (e.g. nitrogen) with dry solvent. The bromo compound is then added under the inert atmosphere with heat to cause refluxing for a short period, 5 to 45 minutes. Then an appropriate amount of acetone is added under a dry, inert atmosphere. Heat is then applied to cause refluxing for about 10 to 60 minutes. Water, which can be in the form of ice, is then added, and the compound purified by standard techniques.

Ring closure (formula 10) is effected by treating the tertiary alcohol with acid, preferably a strong acid like sulfuric acid, at reduced temperature, e.g. $-10°$ to $+10°$ C. After a brief reaction time, the reaction product is recovered by extraction steps commonly used in the art. The resulting 1,1-dimethyl-1,2,3,4-tetrahydronaphthalene is then converted to the two acids, 8,8-dialkyl acid and the 5,5-dialkyl acid, by the steps outlined above under Reaction Scheme I.

Preparation of compounds with the reverse connectivity, that is where A is —OC(O)—, is illustrated in Reaction Scheme III. The phenol, or a corresponding 2-alkyl substituted phenol, is reacted with a tetrahydrofuran in the presence of aluminum chloride (Friedel-Crafts reaction). An alkane or similar type solvent is used. The reaction is effected first at room temperature for up to 5 hours, preferably about 2.5 hours, then at reflux for about an equal period of time. A dilute solution of acid (e.g. 3N HCl) is then added to quench the reaction. Normal isolation techniques are then used to recover the compound.

Terephthallic acids, the acids of Reaction Scheme III, are readily available from most chemical supply houses. They may be esterified and selectively hydrolyzed to the mono-acid. The coupling reaction used to make the final product is the same or an obvious variation of the generalized reaction sequence and conditions given for Reaction Scheme I.

Alcohols are made by converting the corresponding acids of formula I to the acid chloride with thionyl chloride (J. March, "Advanced Organic Chemistry", 2nd Edition, McGraw-Hill Book Company), then reducing the acid chloride with sodium borohydride (March, Ibid, pg. 1124), or by diborane reduction. Alternatively, aldehydes of formula II can be reduced to the alcohol using sodium borohydride.

Aldehydes of formula III compounds can be prepared from the corresponding primary alcohols using mild oxidizing agents such as exemplified by pyridinium dichromate in methylene chloride (Corey, E. J., Schmidt, G., *Tet. Lett.*, 399, 1979). Alkylating these alcohols with appropriate alkyl halides under Williamson reaction conditions (March, Ibid, pg. 357) gives the corresponding ethers.

Acetals can be prepared from the corresponding aldehyde by the method described in March, Ibid, p 810.

EXAMPLE 1

2,5-Dichloro-2,5-dimethylhexane

Hydrogen chloride gas was bubbled through a suspension of 48 g (0.33 mol) of 2,5-dimethyl-2,5-hexanediol (Aldrich) in 600 ml of concentrated HCl until the solution was saturated. The resultant crystalline product was collected by filtration, washed repeatedly with water and dried on a vacuum line to give the title compound as a white crystalline material. PMR (CDCl$_3$): δ 1.60 (12H, s), 1.94 (4H, s).

EXAMPLE 2

1,1,4,4-Tetramethyl-1,2,3,4-tetrahydronaphthalene

A vigorously stirred solution of 100 g (0.55 mol) 2,5-dichloro-2,5-dimethylhexane in 300 ml of benzene was cooled in an ice bath and treated with 45 g (0.34 mol) anhydrous aluminum chloride in small portions. This mixture was stirred at room temperature for 3 hours, refluxed for 1 hour, cooled and poured into a mixture of ice and HCl. The organic layer was separated and the aqueous layer extracted with ether. Organic fractions were combined, washed with water, saturated Na$_2$CO$_3$, saturated NaCl solution and then dried (MgSO$_4$). After removal of solvent, the residue was fractionally distilled (78° C., 0.8 mm) to give the captioned compound as a colorless liquid. PMR (CDCl$_3$): δ 1.3 (12H, s), 1.7 (4H, s), 7.1 (2M, m), 7.5 (2H, m).

EXAMPLE 3

5,5,8,8-Tetramethyl-2-acetyl-5,6,7,8-tetrahydronaphthalene

A suspension of 3.45 g (25.9 mmol) aluminum chloride in 15 ml methylene chloride was cooled under argon in an ice-salt bath and treated with stirring with a mixture of 4 g (21.2 mmol) 1,1,4,4-tetramethyl-1,2,3,4-tetrahydronaphthalene and 1.94 g (24.7 mmol) acetyl chloride via a dropping funnel over a period of thirty minutes. The cooling bath was removed and the mixture stirred for 2 hours, then quenched with ice. The organic layer was separated and the aqueous layer extracted with 2×50 ml methylene chloride. Organic extracts were combined and washed with water and saturated NaHCO$_3$ solution and then dried (MgSO$_4$). Solvent was removed in-vacuo and the residue distilled by the kugelrohr method (90° C.; 0.45 mm) to give the title compound as a colorless oil. PMR (CDCl$_3$): δ 1.32 (6H, s), 1.33 (6H, s), 1.72 (4H, s), 2.60 (3H, s), 7.41 (1H, d, J~8.9 Hz), 7.71 (1H, dd, J~8.8, 2.6 Hz) 7.96 (1H, d, J~2.6 Hz).

EXAMPLE 4

5,5,8,8-Tetramethyl-5,6,7,8-tetrahydro-2-naphthoic acid

A mixture of 3.8 g (16.5 mmol) of 5,5,8,8-tetramethyl-2-acetyl-5,6,7,8-tetrahydronaphthalene from the preceeding Example 3, 70 ml of 5.25% aqueous sodium hypochlorite (49 mmol), 25 ml of aqueous 2N NaOH and 30 ml of dioxane was heated at 60°-70° C. for 2 hours. The mixture was allowed to cool and the oily organic layer removed. Then the aqueous layer was washed with two portions of ether. The aqueous layer was then treated with sodium metabisulfite solution until the solution was negative to the potassium iodide-starch test. The aqueous layer was then cooled and acidified with H$_2$SO$_4$. The resultant white precipitate was collected by filtration and washed with water. This crude product was further purified by recrystallization from an ethanol/water mixture to give the title compound as a white, crystalline solid. PMR (CDCl$_3$): δ 1.31 (6H, s), 1.32 (6H, s), 1.71 (4H, s), 7.40 (1H, d, J~8.8 Hz), 7.85 (1H, dd, J~8.8 Hz, 1.8 Hz), 8.08 (1H, d, J~1.8 Hz).

EXAMPLE 5

Preparation of 4-Substituted Phenolic Esters

A. Pentadeuteroethyl 4-hydroxybenzoate-A mixture of 2.6552 g (19.2238 mmol) of 4-hydroxybenzoic acid, 1 g (19.1864 mmol) of hexadeuteroethanol, 20 ml of benzene and 5 drops of concentrated H$_2$SO$_4$ was heated at reflux for 24 h on an apparatus fitted with a Dean-Stark trap. The solvent was removed and the residue extracted with ether. The ether extract was washed with water, saturated NaHCO$_3$ and saturated NaCl solutions and then dried (MgSO$_4$). Solution was filtered and concentrated in-vacuo. The residue was purified by flash chromatography (silica; 15% ethyl acetate in hexanes) to give the title compound as a white solid. PMR (CDCl$_3$): 6.84 (2H, d, J~8.8 Hz), 7.95 (2H, d, J~8.8 Hz).

Using the same general procedure, but using n-hexanol instead, n-hexyl 4-hydroxybenzoate was synthesized as a colorless, viscous oil. PMR (CDCl$_3$): δ 0.92 (3H, m), 1.36 (6H, m), 1.78 (2H, m), 4.33 (2H, q, J~6.7 Hz), 6.97 (2H, d, J~8.8 Hz), 7.99 (2H, d, J~8.8 Hz).

B. n-Tetradecyl 4-hydroxybenzoate-To a solution of 2.76 g (20 mmol) of 4-hydroxybenzoic acid and 800 mg (200 mmol) of sodium hydroxide in 12 ml of water was added 250 mg of methyl tricaprylammonium chloride and 4.67 g (17 mmol) of n-tetradecylbromide. The mixture was heated at reflux for 4 h and then diluted with 30 ml of water. The mixture was extracted with 2×30 ml ether. The ether extracts were combined and washed with water and saturated NaCl solution. The solvent was removed in-vacuo and the residue purified by flash chromatography (silica; 10% ethyl acetate in hexanes) to give the title compound as a white solid. PMR (CDCl$_3$): δ 0.88 (3H, m), 1.26 (20H, broad s), 1.42 (2H, m), 1.75 (2H, m), 4.29 (2H, t, J~6.6 Hz), 6.90 (2H, d, J~8.8 Hz), 7.96 (2H, d, J~8.8 Hz).

C. Tert-butyl 4-hydroxybenzoate-Excess isobutylene gas was condensed at −78° C. in a high-pressure tube containing 13.8 g (0.1 mol) of 4-hydroxybenzoic acid dissolved in 50 ml of dioxane and 1 ml of conc. H$_2$SO$_4$ was then added to the mixture. The tube was then sealed and the reaction mixture warmed to room temperature and stirred for 2 h. The mixture was then cooled to −78° C. and the tube was opened and its contents poured slowly into an excess of saturated NaHCO$_3$ solution. Any excess isobutylene was removed by means of a nitrogen stream and the mixture was extracted with ether. The ether solution was extracted with 1N NaOH solution and the ether layer was discarded. The aqueous extract was acidified with dilute H$_2$SO$_4$ and then extracted with ether. The ether extract was washed with NaHCO$_3$ solution and then dried (Na$_2$SO$_4$). The solution was filtered and the solvent removed in-vacuo. The residue was purified by flash chromatography (silica; 40% ethyl acetate in hexanes) to give the title compound as a white solid. PMR (CDCl$_3$): δ 1.59 (9H, s), 6.90 (2H, d, J~8.5 Hz), 7.89 (2H, d, J~8.5 Hz), 8.0 (1H, broad s).

D. Ethyl 4-hydroxy-3-methylbenzoate-Ethyl 4-amino-3-methylbenzoate (3.85 g; 21.5 mmol) was dissolved in hot, 35% H$_2$SO$_4$/water and the mixture then cooled to below 5° C. An ice-cold solution of 1.91 g (22.5 mmol) of sodium nitrite in 20 ml of water was then slowly added to the mixture such that the temperature of the mixture never exceeded 5° C. The mixture was stirred at 5° C. for 10 minutes and then treated with 1 g of urea and stirred for a further 10 minutes. A solution of 50 g (207 mmol) of cupric nitrate trihydrate in 750 ml of water was added to the reaction mixture followed by 2.87 g of cuprous oxide. The mixture was stirred for a further 15 minutes and then extracted with 3×300 ml ether. The ether extracts were combined and then washed with water and saturated NaCl solution and then dried (MgSO$_4$). The solution was filtered, the solvent removed in-vacuo and the residue purified by flash chromatography (silica; 13% ethyl acetate in hexanes to 20% ethyl acetate in hexanes) to give the title compound as a pale yellow solid. PMR (CDCl$_3$): δ 1.39 (3H, t, J∼7.1 Hz), 2.28 (3H, s), 4.37 (2H, q, J∼7.1 Hz), 6.87 (1H, d, J∼8.5 Hz), 7.38 (1H, s), 7.79 (1H, dd, J∼8.5 Hz, 2.0 Hz), 7.85 (1H, d, J∼2.0 Hz).

E. Ethyl 4-hydroxy-3,5-dimethylbenzoate-A mixture of 500 mg (3 mmol) of 4-hydroxy-3,5-dimethylbenzoic acid, 20 ml of absolute ethanol and a catalytic amount of anhydrous HCl was heated at reflux for 2 h. The mixture was then poured into excess cold water and the resultant precipitate was filtered. The precipitate was washed with water and dried in-vacuo to give the title compound as a white solid. PMR (CDCl$_3$): δ 1.38 (3H, t, J∼7.0 Hz), 2.27 (6H, s), 4.33 (2H, q, J∼7.0 Hz), 5.30 (1H, broad s), 7.70 (2H, s).

F. 4-Tert-butyldimethylsiloxymethylphenol-A mixture of 1.24 g (0.01 mole) of 4-hydroxymethylphenol, 1.8 g (0.012 mole) of tert-butyldimethylsilyl chloride, 1.7 g (0.025 mole) of imidazole and 3 ml of dimethylformamide was stirred under nitrogen at room temperature for 12 h. The reaction mixture was poured into water and extracted with three portions of ether. Ether extracts were combined and washed successively with water and saturated NaCl solution and then dried (Na$_2$SO$_4$). The ether solution was concentrated in-vacuo and the resultant crude product was purified by flash chromatography (silica; 10% ethyl acetate in hexanes) to give the title compound as a colorless oil. PMR (CDCl$_3$): δ 0.09 (6H, s), 0.93 (9H, s), 4.66 (2H, s), 5.69 (1H, broad s), 6.74 (2H, d, J∼6.9 Hz), 7.16 (2H, d, J∼6.9 Hz).

G. 4-Dimethoxymethylphenol-A mixture of 4.88 g (40 mmol) of 4-hydroxybenzaldehyde, 6.6 g (206 mmol) of methanol and 5.1 g (48 mmol) of trimethylorthoformate and 28 mg of p-toluene sulfonic acid was stirred at room temperature for 12 h. An excess of NaHCO$_3$ was then added and the mixture stirred for a further 60 h. The mixture was then filtered, the solvent removed in-vacuo and the residue purified by flash chromatography (silica; 20% ethyl acetate in hexanes) to give the title compound as a viscous oil. PMR (CDCl$_3$): δ 3.26 (6H, s), 5.38 (1H, s), 6.82 (2H, d, J∼8.5 Hz), 7.31 (2H, d, J∼8.5 Hz), 7.36 (1H, broad s).

EXAMPLE 6

Ethyl 4-(5,5,8,8-tetramethyl-5,6,7,8-tetrahydro-2-naphthoyloxy)benzoate

A solution of 116 mg (0.5 mmol) of 5,5,8,8-tetramethyl-5,6,7,8-tetrahydro-2-naphthoic acid, 58 mg (0.5 mmol) of ethyl 4-hydroxybenzoate, 117 mg (0.56 mmol) of 1,3-dicyclohexylcarbodiimide and 30 mg (0.25 mmol) of 4-dimethylaminopyridine in 15 ml of methylene chloride was stirred at room temperature for 12 hours. The reaction mixture was then filtered and the filtrate concentrated in-vacuo. The resultant residue was purified by flash chromatography (silica; 5% ethyl acetate in hexanes) to give the title compound as white crystals. PMR (CDCl$_3$): δ 1.32 (6H, s), 1.36 (6H, s), 1.42 (3H, t, J∼7.0 Hz), 1.73 (4H, s), 4.40 (2H, q, J∼7.0 Hz), 7.28 (2H, d, J∼8.1 Hz), 7.45 (1H, d, J∼8.8 Hz), 7.93 (1H, dd, J∼8.8 Hz, 1.8 Hz), 8.13 (2H, d, J∼8.1 Hz), 8.14 (1H, s).

Using the same general procedure and materials, but substituting the appropriate phenol for ethyl 4-hydroxybenzoate, the following compounds were synthesized:

A. Benzyl 4-(5,5,8,8-tetramethyl-5,6,7,8-tetrahydro-2-naphthoyloxy)benzoate-Using benzyl 4-hydroxybenzoate, the title compound was synthesized as a white, crystalline solid. PMR (CDCl$_3$): δ 1.32 (6H, s), 1.35 (6H, s), 1.72 (4H, s), 5.38 (2H, s), 7.24–7.48 (8H, m), 7.92 (1H, dd, J∼8.8 Hz, 1.8 Hz), 8.12–8.20 (3H, m).

B. Pentadeuteroethyl 4-(5,5,8,8-tetramethyl-5,6,7,8-tetrahydro-2-naphthoyloxy)benzoate-Using pentadeuteroethyl 4-hydroxybenzoate, the captioned compound was synthesized as a colorless oil. PMR (CDCl$_3$): δ 1.33 (6H, s), 1.36 (6H, s), 1.73 (4H, s), 7.30 (2H, d, J∼8.7 Hz), 7.46 (1H, d, J∼8.3 Hz), 7.96 (1H, dd, J∼8.3 Hz, 1.8 Hz), 8.15 (2H, d, J∼8.7 Hz), 8.18 (1H, d, J∼1.8 Hz).

C. n-Hexyl 4-(5,5,8,8-tetramethyl-5,6,7,8-tetrahydro-2-naphthoyloxy)benzoate-Using n-hexyl 4-hydroxybenzoate, the title compound was synthesized as a colorless oil. PMR (CDCl$_3$): δ 0.92 (3H, m), 1.33 (6H, s), 1.35 (6H, s), 1.42 (6H, m), 1.74 (4H, s), 1.77 (2H, m), 4.34 (2H, t, J∼6.7 Hz), 7.30 (2H, d, J∼8.8 Hz), 7.46 (1H, d, J∼8.3 Hz)), 7.95 (1H, dd, J∼8.3 Hz, 1.9 Hz), 8.14 (2H, d, J∼8.8 Hz), 8.17 (1H, d, J∼1.9 Hz).

D. n-Tetradecyl 4-(5,5,8,8-tetramethyl-5,6,7,8-tetrahydro-2-naphthoyloxy)benzoate-Using n-tetradecyl 4-hydroxybenzoate, the title compound was synthesized as a colorless oil. PMR (CDCl$_3$): δ 0.83–0.94 (3H, m), 1.15–1.50 (34H, m), 1.70–1.85 (6H, m), 4.34 (2H, t, J∼6.7 Hz), 7.29 (2H, d, J∼8.7 Hz), 7.46 (1H, d, J∼8.4 Hz), 7.95 (1H, dd, J∼8.4 Hz, 1.8 Hz), 8.14 (2H, d, J∼8.7 Hz), 8.16 (1H, d, J∼1.8 Hz).

E. tert-Butyl 4-(5,5,8,8-tetramethyl-5,6,7,8-tetrahydro-2-naphthoyloxy)benzoate-Using tert-butyl 4-hydroxybenzoate, the title compound was synthesized as a white solid. PMR (CDCl$_3$): δ 1.33 (6H, s), 1.35 (6H, s), 1.62 (9H, s), 1.73 (4H, s), 7.25 (2H, d, J∼8.7 Hz), 7.45 (1H, d, J∼8.4 Hz), 7.93 (1H, dd, J∼8.4 Hz, 1.8 Hz), 8.07 (2H, d, J∼8.7 Hz), 8.15 (1H, d, J∼1.8 Hz).

F. Ethyl 4-(5,5,8,8-tetramethyl-5,6,7,8-tetrahydro-2-naphthoyloxy)-3-methylbenzoate-Using ethyl 4-hydroxy-3-methylbenzoate, the title compound was synthesized as a white solid. PMR (CDCl$_3$): δ 1.34 (6H, s), 1.36 (6H, s), 1.41 (3H, t, J∼7.2 Hz), 1.74 (4H, s), 2.30 (3H, s), 4.39 (2H, t, J∼7.2 Hz), 7.22 (1H, d, J∼8.4 Hz), 7.47 (1H, d, J∼8.3 Hz), 7.94–8.04 (3H, m), 8.19 (1H, d, J∼1.7 Hz).

G. Ethyl 4-(5,5,8,8-tetramethyl-5,6,7,8-tetrahydro-2-naphthoyloxy)-3,5-dimethylbenzoate-Using ethyl 4-hydroxy-3,5-dimethylbenzoate, the title compound was synthesized as a white solid. PMR (CDCl$_3$): δ 1.37 (6H, s), 1.39 (6H, s), 1.44 (3H, t, J∼7.0 Hz), 1.77 (4H, s), 2.27 (6H, s), 4.41 (2H, q, J∼7.0 Hz), 7.50 (1H, d, J∼8.4 Hz), 7.86 (2H, s), 8.03 (1H, dd, J∼8.4 Hz, 2.0 Hz), 8.23 (1H, d, J∼2.0 Hz).

H. 4-(5,5,8,8-Tetramethyl-5,6,7,8-tetrahydro-2-naphthoyloxy)benzamide-Using 4-hydroxybenzamide, the title compound was synthesized as a white solid. PMR (CDCl$_3$): δ 1.35 (6H, s), 1.37 (6H, s), 1.76 (4H, s), 7.32 (2H, d, J∼8.6 Hz), 7.48 (1H, d, J∼8.4 Hz), 7.89–7.98 (3H, m), 8.17 (1H, d, J∼1.9 Hz).

I. 4-Methoxymethylphenyl 5,5,8,8-tetramethyl-5,6,7,8-tetrahydro-2-naphthoate-Using 4-methoxymethylphenol, the title compound was synthesized as a colorless oil. PMR (CDCl$_3$): δ 1.36 (6H, s), 1.38 (6H, s), 1.76 (4H, s), 3.44 (3H, s), 4.52 (2H, s), 7.22 (2H, d, J∼8.4 Hz), 7.43 (2H, d, J∼8.4 Hz), 7.48 (1H, d, J∼8.4 Hz), 7.97 (1H, dd, J∼8.4 Hz, 1.5 Hz), 8.19 (1H, d, J∼1.5 Hz).

J. 4-tert-butyldimethylsiloxymethylphenyl 5,5,8,8-tetramethyl-5,6,7,8-tetrahydro-2-naphthoate Using 4-tert-butyldimethylsiloxymethylphenol, the title compound was synthesized as a white solid. PMR (CDCl$_3$): δ 0.14 (6H, s), 0.98 (9H, s), 1.34 (6H, s), 1.37 (6H, s), 1.75 (4H, s), 4.79 (2H, s), 7.18 (2H, d, J∼9.0 Hz), 7.40 (2H, d, J∼9.0 Hz), 7.46 (1H, d, J∼8.4 Hz), 7.88 (1H, dd, J∼8.4 Hz, 1.7 Hz), 8.18 (1H, d, J∼1.7 Hz).

K. 4-Formylphenyl 5,5,8,8-tetramethyl-5,6,7,8-tetrahydro-2-naphthoate-Using 4-hydroxybenzaldehyde, the title compound was synthesized as a white solid. PMR (CDCl$_3$): δ 1.32 (6H, d), 1.34 (6H, s), 1.73 (4H, s), 7.39 (2H, d, J∼9.0 Hz), 7.45 (1H, d, J∼8.4 Hz), 7.92–7.98 (3H, m), 8.16 (1H, d, J∼1.8 Hz), 9.99 (1H, s).

L. 4-Acetylphenyl 5,5,8,8-tetramethyl-5,6,7,8-tetrahydro-2-naphthoate-Using 4-acetylphenol, the title compound was synthesized as a white solid. PMR (CDCl$_3$): δ 1.36 (6H, s), 1.38 (6H, s), 1.76 (4H, s), 2.64 (3H, s), 7.34 (2H, d, J∼8.4 Hz), 7.48 (1H, d, J∼8.4 Hz), 7.98 (1H, dd, J∼8.4 Hz, 2.4 Hz), 8.07 (2H, d, J∼8.4 Hz), 8.19 (1H, d, J∼2.4 Hz).

M. 4-Dimethoxymethylphenyl-5,5,8,8-tetramethyl-5,6,7,8-tetrahydro-2-naphthoate-Using 4-dimethoxymethylphenol, the title compound was synthesized as a colorless oil. PMR (CDCl$_3$): δ 1.32 (6H, s), 1.34 (6H, s), 1.72 (4H, s), 3.34 (6H, s), 5.44 (1H, s), 7.21 (2H, d, J∼8.4 Hz), 7.44 (1H, d, J∼8.4 Hz), 7.52 (2H, d, J∼8.4 Hz), 7.94 (1H, dd, J∼8.4 Hz, 1.8 Hz), 8.16 (1H, d, J∼1.8 Hz).

N. 4-Ethoxyphenyl 5,5,8,8-tetramethyl-5,6,7,8-tetrahydro-2-naphthoate-Using 4-ethoxyphenol, the title compound was synthesized as a white solid. PMR (CDCl$_3$): δ 1.32 (6H, s), 1.34 (6H, s), 1.42 (3H, t, J∼7.0 Hz), 1.72 (4H, s), 4.04 (2H, q, J∼7.0 Hz), 6.92 (2H, d, J∼9.0 Hz), 7.10 (2H, d, J∼9.0 Hz), 7.43 (1H, d, J∼8.3 Hz), 7.93 (1H, dd, J∼8.3 Hz, 1.9 Hz), 8.15 (1H, d, J∼1.9 Hz).

O. 4-Benzyloxyphenyl 5,5,8,8-tetramethyl-5,6,7,8-tetrahydro-2-naphthoate-Using 4-benzyloxyphenol, the title compound was synthesized as a white solid. PMR (CDCl$_3$): δ 1.32 (6H, s), 1.34 (6H, s), 1.72 (4H, s), 5.07 (2H, s), 7.00 (2H, d, J∼9.3 Hz), 7.11 (2H, d, J∼9.3 Hz), 7.31–7.47 (6H, m), 7.92 (1H, dd, J∼8.4 Hz, 1.9 Hz), 8.14 (1H, d, J∼1.9 Hz).

P. p-Toluyl 5,5,8,8-tetramethyl-5,6,7,8-tetrahydro-2-naphthoate-Using p-cresol, the title compound was synthesized as a white solid. PMR (CDCl$_3$): δ 1.34 (6H, s), 1.36 (6H, s), 1.74 (4H, s), 2.39 (3H, s), 7.09 (2H, d, J∼8.4 Hz), 7.23 (2H, d, J∼8.4 Hz), 7.45 (1H, d, J∼8.3 Hz), 7.95 (1H, dd, J∼8.3 Hz, 1.9 Hz), 8.17 (1H, d, J∼1.9 Hz).

Q. Phenyl 5,5,8,8-tetramethyl-5,6,7,8-tetrahydro-2-naphthoate-Using phenol, the title compound was synthesized as a white solid. PMR (CDCL$_3$): δ 1.35 (6H, s), 1.38 (6H, s), 1.76 (4H, s), 7.21–7.32 (3H, m), 7.41–7.50 (3H, m), 7.99 (1H, dd, J∼8.5 Hz, 1.8 Hz), 8.21 (1H, d, J∼1.8 Hz).

EXAMPLE 7

4-(5,5,8,8-Tetramehtyl-5,6,7,8-tetrahydro-2-naphthoyloxy)benzoic acid

A mixture of 150 mg (0.3394 mmol) of benzyl 4-(5,5,8,8-tetramethyl-5,6,7,8-tetrahydro-2-naphthoyloxy)benzoate and 50 mg of 10% palladium on carbon in 5 ml of ethyl acetate was stirred under a hydrogen atmosphere at room temperature for 4 hours. The reaction mixture was then filtered and the filtrate was concentrated in-vacuo. The residue was dissolved in ether and extracted with aqueous NaOH solution. The aqueous extract was then acidified with glacial acetic acid and extracted with ether. The ether extract was washed with saturated NaCl solution and then concentrated in-vacuo. The resultant residue was recrystallized from ethyl acetate to give the title compound as a white solid. PMR (CDCl$_3$): δ 1.34 (6H, s), 1.36 (6H, s), 1.76 (4H, s), 7.33 (2H, d, J∼8.6 Hz), 7.46 (1H, d, J∼7.8 Hz), 7.94 (1H, dd, J∼7.8 Hz, 1.8 Hz), 8.16 (1H, d, J∼1.8 Hz), 8.21 (2H, d, J∼8.6 Hz).

EXAMPLE 8

1,1,4,4,6-Pentamethyl-1,2,3,4-tetrahydronaphthalene

To a cooled (0° C.) mixture of 40 g (0.4341 mol) toluene and 25 g (0.195 mol) 2,2,5,5-tetramethyltetrahydrofuran was added in small portions with stirring 26.6 g (0.2 mol) of anhydrous aluminum chloride. The cooling bath was removed and the mixture stirred at room temperature for 20 h and then heated at reflux for 2 hours. This mixture was allowed to cool to room temperature and then the reaction quenched by pouring into a mixture of ice and 100 ml 3N HCl. The organic layer was separated and the aqueous layer extracted with 3×75 ml ether. The organic extracts were combined and washed with 3N HCl, saturated NaHCO$_3$, saturated NaCl solution and dried (MgSO$_4$). Solvent was removed in-vacuo and the residue was fractionally distilled to give the captioned compound as a colorless oil. PMR (CDCl$_3$): 1.30 (6H, s), 1.32 (6H, s), 1.70 (4H, s), 2.33 (3H, s), 6.98 (1H, d, J∼7 Hz), 7.14 (1H, s), 7.23 (1H, d, J∼7 Hz).

EXAMPLE 9

2-Acetyl-3,5,5,8,8-pentamethyl-5,6,7,8-tetrahydronaphthalene

To a suspension of 13.72 g (102.9 mmol) aluminum chloride in 40 ml dichloroethane, which was cooled in an ice-acetone bath under argon, was added with stirring over 1 h a solution of 17.11 g (84.56 mmol) of 1,1,4,4,6-pentamethyl-1,2,3,4-tetrahydronaphthtalene in 10 ml dichloroethane. The cooling bath was removed and the mixture stirred at room temperature for 3 hours, then poured onto ice. The organic layer was separated and the aqueous layer extracted with 3×75 ml methylene chloride. The organic layers were combined and washed several times with water, saturated NaHCO$_3$, saturated NaCl solution and then dried (MgSO$_4$). Solvent was removed in-vacuo and residue subjected to kugelrohr distillation (70° C., 0.15 mm) to give the captioned compound as a low-melting yellow solid. PMR (CDCl$_3$): δ 1.30 (6H, s), 1.32 (6H, s), 1.70 (4H, s), 2.51 (3H, s), 2.59 (3H, s), 7.16 (1H, s), 7.69 (1H, s).

EXAMPLE 10

3,5,5,8,8-Pentamethyl-5,6,7,8-tetrahydro-2-naphthoic acid

A mixture of 8.2 g (0.0336 mol) of 2-acetyl-3,5,5,8,8-pentamethyl-5,6,7,8-tetrahydronaphthalene, 90 ml of 1.19M (0.107 mol) aqueous sodium hypochlorite and 10 ml of dioxane was stirred at room temperature for 0.5 hours and at 60° C. for 2 hours. A further 70 ml of 1.19M (0.0833 mol) of aqueous sodium hypochlorite was then added to the reaction mixture and the mixture stirred at 70° C. for 1 hours. The reaction mixture was then cooled and treated with aqueous sodium bisulfite solution until the mixture was negative to starch/iodide paper. The mixture was washed with ether and then acidified with H$_2$SO$_4$. The mixture was extracted with three portions of ether and the ether extracts were then combined and washed successively with water and saturated NaCl solution and then dried (MgSO$_4$). The ether solution was then concentrated and the title compound obtained as colorless crystals by recrystallization from cold ether. PMR (CDCl$_3$): δ 1.29 (6H, s), 1.30 (6H, s), 1.69 (4H, s), 2.60 (3H, s), 7.17 (1H, s), 7.26 (1H, s).

EXAMPLE 11

Ethyl 4-(3,5,5,8,8-pentamethyl-5,6,7,8-tetrahydro-2-naphthoyloxy)benzoate

A mixture of 399.2 mg (1.6204 mmol) of 3,5,5,8,8-pentamethyl-5,6,7,8-tetrahydro-2-naphthoic acid, 271.8 mg (1.6355 mmol) of ethyl 4-hydroxybenzoate, 336.6 mg (1.6339 mmol) of 1,3-dicyclohexylcarbodiimide and 44.5 mg (0.3642 mmol) of 4-dimethylaminopyridine in 20 ml of methylene chloride was stirred at room temperature for 23 h. The reaction mixture was filtered and the residue washed with 25 ml of methylene chloride. The filtrate was concentrated in-vacuo and the resultant crude product was purified by flash chromatography (silica; 10% ethyl acetate in hexanes) to give the title compound as a white solid. PMR (CDCl$_3$): δ 1.34 (6H, s), 1.36 (6H, s), 1.43 (3H, t, J~7.2 Hz), 1.74 (4H, s), 2.66 (3H, s), 4.42 (2H, q, J~7.2 Hz), 7.26 (1H, s), 7.31 (2H, d, J~8.7 Hz), 8.16 (2H, d, J~8.7 Hz), 8.17 (1H, s).

Using the same general procedure and using instead benzyl 4-hydroxybenzoate, benzyl 4-(3,5,5,8,8-pentamethyl-5,6,7,8-tetrahydro-2-naphthoyloxy)benzoate was synthesized as a colorless oil. PMR (CDCl$_3$: δ 1.32 (6H, s), 1.35 (6H, s), 1.72 (4H, s), 2.63 (3H, s), 5.39 (2H, s), 7.24 (1H, s), 7.29 (2H, d, J~8.4 Hz), 7.34–7.49 (5H, m), 8.14 (1H, s), 8.18 (2H, d, J~8.4 Hz).

Using the same general procedure but using instead 4-methoxymethylphenol, 4-methoxymethylphenyl 3,4,5,8,8-pentamethyl-5,6,7,8-tetrahydro-2-naphthoate was synthesized as a colorless oil. PMR (CDCl$_3$): δ 1.34 (6H, s), 1.37 (6H, s), 1.74 (4H, s), 2.66 (3H, s), 3.43 (3H, s), 4.52 (2H, s), 7.21 (1H, s), 7.22 (2H, d, JN8.3 Hz), 7.26 (1H, s), 7.43 (2 h, d, JN8.3 Hz), 8.17 (1H, s).

EXAMPLE 12

4-(3,5,5,8,8-Pentamethyl-5,6,7,8-tetrahydro-2-naphthoyloxy)benzoic acid

A mixture of 430 mg (0.94 mmol) of benzyl 4-(3,5,5,8,8-pentamethyl-5,6,7,8-tetrahydro-2-naphthoyloxy)benzoate, 60 mg of 10% palladium on carbon and 6 ml of ethyl acetate was stirred under a hydrogen atmosphere at room temperature for 3 hours. A further 6 ml of ethyl acetate was then added to the reaction mixture and mixture heated at 50° C. for 3 hours. The reaction mixture was then cooled, filtered through celite and the residue washed with 5 ml of warm ethyl acetate. The filtrate was then concentrated in-vacuo and the resultant residue recrystallized from a mixture of ethyl acetate and hexanes to give the title compound as a white, crystalline solid. PMR (CDCl$_3$): δ 1.32 (6H, s), 1.34 (6H, s), 1.72 (4H, s), 2.62 (3H, s), 7.24 (1H, s), 7.32 (2H, d, J~8.2 Hz), 8.13 (1H, s), 8.20 (2H, d, J~8.2 Hz).

EXAMPLE 13

2-Methyl-5-phenyl-2-pentanol

A mixture of 8.8 g. (0.37 mol.) of magnesium turnings and 150 ml of dry ether was placed in a 3-necked flask fitted with a nitrogen inlet, a reflux condenser and an addition funnel containing 73.7 g (0.37 mol) of 1-bromo-3-phenylpropane. A small amount of the bromo compound was added to the reaction mixture and the mixture warmed in order to initiate reaction. The reaction mixture was treated with 150 ml of dry ether and then the bromo compound was added at such a rate as to maintain gentle reflux. The reaction mixture was heated at reflux for a further 15 minutes and then treated slowly with 21.5 g (0.37 mol) of acetone. The mixture was heated at reflux for a further 30 minutes, cooled and then poured slowly into 300 g of crushed ice. The resultant white precipitate was dissolved by the addition of 20% H$_2$SO$_4$. The organic layer was separated and the aqueous layer extracted with ether. The organic extracts were combined and washed with water and saturated NaCl solution and then dried (MgSO$_4$). The solution was filtered and the solvent removed in-vacuo. The residue was distilled (120° C.; 6 mm) to give the captioned compound as a colorless oil. PMR (CDCl$_3$): δ 1.18 (6H, s), 1.44–1.53 (2H, m), 1.62–1.72 (2H, m), 2.61 (2H, t, J~7.6 Hz), 7.16–7.30 (5H, m).

EXAMPLE 14

1,1-Dimethyl-1,2,3,4-tetrahydronaphthalene

To 18 ml of ice-cold concentrated H$_2$SO$_4$ was added 17.8 g (0.1 mol) of 2-methyl-5-phenyl-2-pentanol over 10 minutes. The mixture was then stirred at 0° C. for 15 minutes and at room temperature for 15 minutes. The mixture was treated with 50 ml of water and then extracted with ether. The ether extracts were combined and washed with water and saturated NaCl and NaHCO$_3$ solutions and then dried (MgSO$_4$). The solution was filtered and the solvent removed in-vacuo. The residue was purified by distillation (93° C.; 10 mm) to give the title compound as a colorless oil. PMR (CDCl$_3$): δ 1.19 (6H, s), 1.45–1.53 (2H, m), 1.62–1.73 (2H, m), 2.62 (2H, t, J~6.1 Hz), 7.14–7.30 (4H, m).

EXAMPLE 15

2-(1-hydroxyethyl)-8,8-dimethyl-5,6,7,8-tetrahydronaphthalene and
2-(1-hydroxyethyl)-5,5-dimethyl-5,6,7,8-tetrahydronaphthalene A solution of 4.0 g (25 mmol) of 1,1-dimethyl-1,2,3,4-tetrahydronaphthalene and 2.35 g (30 mmol) of acetyl chloride in 5 ml of methylene chloride was added slowly to a stirred suspension of 4.27 g (32 mmol) of anhydrous aluminum chloride in 15 ml of methylene chloride at 0° C. After approximately half the solution had been added, the cooling bath was removed and the addition completed at room temperature. The reaction mixture was then stirred for 1 hour and poured into 70 ml of ice-water mixture. The organic layer was separated and washed successively with dilute HCl, water and saturated NaCl solution and then dried (MgSO$_4$). The solution was filtered and the solvent removed in-vacuo and the residue distilled (100° C.; 0.1 mm) to give an approximately 2:1 mixture of the ketones, 2-acetyl-8,8-dimethyl-5,6,7,8-tetrahydronaphthalene and 2-acetyl-5,5-dimethyl-5,6,7,8-tetrahydronaphthalene, as a colorless oil.

A solution of 4.0 g (19.8 mmol) of the mixture of ketones, prepared above, in 10 ml of dry ether was added slowly to a stirred mixture of 250 mg (6.7 mmol) of lithium aluminum hydride in 30 ml of dry ether. The reaction mixture was heated at reflux for 0.5 h and then cooled and the excess lithium aluminum hydride destroyed by the careful addition of ethyl acetate. Water was then added to the mixture followed by sufficient dilute HCl to dissolve any precipitate. The organic layer was separated and washed successively with water and saturated NaCl solution and then dried (MgSO$_4$). The solution was filtered and the solvent removed in-vacuo. The residue was purified by distillation (115° C.; 1 mm) followed by high pressure liquid chromatography (Whatman M20 Partisil column; 10% ethyl acetate in hexanes; 9.9 ml/min) to give the pure title compounds as colorless viscous oils.

PMR (CDCl$_3$) for 2-(1-hydroxyethyl)-8,8-dimethyl-5,6,7,8-tetrahydronaphthalene: δ 1.28 (3H, s), 1.29 (3H, s), 1.47 (3H, d, J∼6.6 Hz), 1.61–1.70 (2H, m), 1.72–1.83 (2H, m), 2.75 (2H, t, J∼6.3 Hz), 4.82 (1H, q, J∼6.6 Hz), 7.02 (1H, d, J∼7.8 Hz), 7.08 (1H, dd, J∼7.8 Hz, 1.8 Hz), 7.32 (1H, d, J∼1.8 Hz).

PMR (CDCl$_3$) for 2-(1-hydroxyethyl)-5,5-dimethyl-5,6,7,8-tetrahydronaphthalene: δ 1.28 (6H, s), 1.47 (3H, d, J∼6.6 Hz), 1.60–1.68 (2H, m), 1.72–1.83 (2H, m), 2.74 (2H, t, J∼6.4 Hz), 4.78 (1H, q, J∼6.6 Hz), 7.03 (1H, d, J∼1.8 Hz), 7.11 (1H, dd, J∼8.1 Hz, 1.8 Hz), 7.29 (1H, d, J∼8.1 Hz).

EXAMPLE 16

2-Acetyl-8,8-dimethyl-5,6,7,8-tetrahydronaphthalene

To a stirred solution of 2.44 g (11.96 mmol) of 2-(1-hydroxyethyl)-8,8-dimethyl-5,6,7,8-tetrahydronaphthalene in 35 ml of methylene chloride was added 6.75 g (17.9 mmol) of pyridinium dichromate and 330 mg (1.68 mmol) of pyridinium trifluoroacetate. The mixture was stirred at room temperature for 24 h and then diluted with 35 ml of low-boiling petroleum ether. The mixture was filtered through a short column of anhydrous MgSO$_4$ and silica and the filtrate then concentrated in-vacuo to give the title compound as a colorless oil. PMR (CDCl$_3$): δ 1.30 (6H, s), 1.60–1.70 (2H, m), 1.72–1.84 (2H, m), 2.56 (3H, s), 2.78 (2H, t, J∼6.1 Hz), 7.08 (1H, d, J∼7.8 Hz), 7.61 (1H, dd, J∼7.8 Hz, 1.9 Hz), 7.93 (1H, d, J∼1.9 Hz).

Using the same general procedure, but using instead 2-(1-hydroxyethyl)-5,5-dimethyl-5,6,7,8-tetrahydronaphthalene, the ketone, 2-acetyl-5,5-dimethyl-5,6,7,8-tetrahydronaphthalene was synthesized as a colorless oil. PMR (CDCl$_3$): δ 1.29 (6H, s), 1.64–1.70 (2H, m), 1.76–1.87 (2H, m), 2.55 (3H, s), 2.81 (2H, t, J∼6.1 Hz), 7.40 (1H, d, J∼8.4 Hz), 7.64 (1H, d, J∼1.8 Hz), 7.71 (1H, dd, J∼8.4 Hz, 1.8 Hz).

EXAMPLE 17

8,8-Dimethyl-5,6,7,8-tetrahydro-2-naphthoic acid

A mixture of 1.0 g (4.95 mmol) of 2-acetyl-8,8-dimethyl-5,6,7,8-tetrahydronaphthalene, 1.8 g of sodium hydroxide, 62 ml of 10% sodium hypochlorite solution, 10 ml of water and 15 ml of dioxane was heated at 65° C. until thin layer chromatography analysis (silica; 10% ethyl acetate in hexanes) indicated absence of starting ketone. The mixture was cooled to room temperature and sodium metabisulphite added until solution was negative to starch-iodide paper. The mixture was then acidified (pH=4) with dilute H$_2$SO$_4$ and the resultant precipitate was filtered, washed with water and dried under vacuum to give the captioned compound as a white solid. PMR (CDCl$_3$): δ 1.32 (6H, s), 1.64–1.72 (2H, m), 1.78–1.88 (2H, m), 2.82 (2H, t, J∼6.1 Hz), 7.14 (1H, d, J∼8.4 Hz), 7.80 (1H, dd, J∼8.4 Hz, 1.8 Hz), 8.10 (1H, d, J∼1.8 Hz).

Using the same general procedure, but using instead 2-acetyl-5,5-dimethyl-5,6,7,8-tetrahydronaphthalene, the acid, 5,5-dimethyl-5,6,7,8-tetrahydro-2-naphthoic acid was synthesized as a white solid. PMR (CDCl$_3$): δ 1.30 (6H, s), 1.64–1.71 (2H, m), 1.75–1.84 (2H, t, J∼6.1 Hz), 7.40 (1H, d, J∼8.3 Hz), 7.81 (1H, d, J∼1.8 Hz), 7.85 (1H, dd, J∼8.3 Hz, 1.8 Hz).

EXAMPLE 18

Ethyl 4-(8,8-dimethyl-5,6,7,8-tetrahydro-2-naphthoyloxy)-benzoate

A solution of 220.7 mg (1.0804 mmol) of 8,8-dimethyl-5,6,7,8-tetrahydro-2-naphthoic acid, 180.6 mg (1.0868 mmol) of ethyl 4-hydroxybenzoate, 227.3 mg (1.1034 mmol) of 1,3-dicyclohexylcarbodiimide and 22.9 mg (0.1874 mmol) of 4-dimethylaminopyridine in 15 ml of methylene chloride was stirred at room temperature for 18 h. The reaction mixture was then filtered and the residue washed with 10 ml of methylene chloride. The filtrate was concentrated in-vacuo and the resultant crude product purified by flash chromatography (silica; 5% ethyl acetate in hexanes) to give the title compound as a colorless oil. PMR (CDCl$_3$): δ 1.35 (6H, s), 1.42 (3H, t, J∼7.2 Hz), 1.68–1.76 (2H, m), 1.80–1.92 (2H, m), 2.85 (2H, t, J∼6.1 Hz), 4.40 (2H, q, J∼7.2 Hz), 7.18 (1H, d, J∼8.0 Hz), 7.31 (2H, d, J∼8.7 Hz), 7.89 (1H, dd, J∼8.0 Hz, 1.6 Hz), 8.11–8.22 (3H, m).

Using the same general procedure, but using benzyl 4-hydroxybenzoate instead, benzyl 4-(8,8-dimethyl-5,6,7,8-tetrahydro-2-naphthoyloxy)benzoate was synthesized, a colorless oil. PMR (CDCl$_3$): δ 1.36 (6H, s), 1.68–1.77 (2H, m), 1.80–1.92 (2H, m), 2.86 (2H, t, J∼6.3 Hz), 5.40 (2H, s), 7.19 (1H, d, J∼8.0 Hz), 7.29–7.51 (7H, m), 7.90 (1H, d, J∼8.0 Hz), 8.15–8.23 (3H, m).

Using the same general procedure, but using instead 5,5-dimethyl-5,6,7,8-tetrahydro-2-naphthoic acid and ethyl 4-hydroxybenzoate, ethyl 4-(5,5-dimethyl-5,6,7,8-tetrahydro-2-naphthoyloxy)benzoate was synthesized as a colorless oil. PMR (CDCl$_3$): δ 1.33 (6H, s), 1.41 (3H, t, J∼7.2 Hz), 1.68–1.76 (2H, m), 1.80–1.90 (2H, m), 2.85 (2H, t, J∼6.3 Hz), 4.39 (2H, q, J∼7.2 Hz), 7.28 (2H, d, J∼8.7 Hz), 7.47 (1H, d, J∼8.4 Hz), 7.90 (1H, s), 7.94 (1H, d, J∼8.4 Hz), 8.13 (2H, d, J∼8.7 Hz).

Using the same general procedure, but using instead 5,5-dimethyl-5,6,7,8-tetrahydro-2-naphthoic acid and benzyl 4-hydroxybenzoate, benzyl 4-(5,5-dimethyl- 5,6,7,8-tetrahydro-2-naphthoyloxy)benzoate was synthesized, as a white solid. PMR (CDCl$_3$): δ 1.37 (6H, s), 1.71–1.78 (2H, m), 1.82–1.92 (2H, m), 2.88 (2H, t, J~6.3 Hz), 5.42 (2H, s), 7.33 (2H, d, J~8.7 Hz), 7.37–7.53 (5H, m), 7.95 (1H, s), 7.99 (1H, d, J~8.4 Hz), 8.20 (2H, d, J~8.7 Hz).

EXAMPLE 19

4-(8,8-Dimethyl-5,6,7,8-tetrahydro-2-naphthoyloxy)-benzoic acid

A mixture of 120 mg (0.29 mmol) of benzyl 4-(8,8-dimethyl-5,6,7,8-tetrahydro-2-naphthoyloxy)benzoate, 50 mg of 10% palladium on activated carbon and 3 ml of ethyl acetate was stirred under a hydrogen atmosphere at room temperature for 2 hour. The mixture was then centrifuged and the supernatant solution decanted. The solvent was then removed in-vacuo and the residue recrystallized from ethyl acetate to give the captioned compound as white crystals. PMR (CDCl$_3$): δ 1.34 (6H, s), 1.67–1.75 (2H, m), 1.78–1.90 (2H, m), 2.85 (2H, t, J~6.0 Hz), 7.18 (1H, d, J~8.1 Hz), 7.34 (2H, d, J~8.7 Hz), 7.88 (1H, dd, J~8.1 Hz, 1.8 Hz), 8.16 (1H, d, J~1.8 Hz), 8.20 (2H, d, J~8.7 Hz). Using the same general procedure, but using benzyl 4-(5,5-dimethyl-5,6,7,8-tetrahydro-2-naphthoyloxy)-benzoate instead, 4-(5,5-dimethyl-5,6,7,8-tetrahydro-2-naphthoyloxy)benzoic acid was synthesized as white crystals. PMR (CDCl$_3$): δ 1.33 (6H, s), 1.67–1.74 (2H, m), 1.78–1.89 (2H, m), 2.86 (2H, t, J~6.3 Hz), 7.33 (2H, d, J~8.8 Hz), 7.47 (1H, d, J~8.1 Hz), 7.90 (1H, d, J~1.8 Hz), 7.95 (1H, dd, J~8.1 Hz, 1.8 Hz), 8.20 (2H, d, J~8.8 Hz).

EXAMPLE 20

5,5,8,8-Tetramethyl-5,6,7,8-tetrahydro-2-naphthol

To a stirred solution of 13.2 g (0.1403 mol) of phenol and 12.8 g (0.0998 mol) of 2,2,5,5-tetramethyltetrahydrofuran in 50 ml of heptane was added 13.1 g (0.0982 mol) of aluminum chloride in small portions. After the addition was complete the mixture was stirred at room temperature for 2.5 hours, at reflux for 2 hours and then at room temperature for a further 16 hours. The reaction mixture was then treated with 100 ml of 3N HCl and stirred for 0.5 hours. The mixture was filtered and the residue washed with water and dried in-vacuo to give crude product. The organic layer was separated from the filtrate and the aqueous layer extracted with 3×75 ml of ether. The organic layers were combined and washed with saturated NaCl solution, dried (MgSO$_4$) and then concentrated in-vacuo to give further crude product. The crude product was recrystallized from hexanes to give the title compound as pale brown crystals. PMR (CDCl$_3$): δ 1.26 (6H, s), 1.28 (6H, s), 1.67 (4H, s), 5.08 (1H, broad s), 6.68 (1H, dd, J~8.7 Hz, 2.7 Hz), 6.82 (1H, d, J~2.7 Hz), 7.16 (1H, d, J~8.7 Hz).

EXAMPLE 21

Diethyl terephthalate

Hydrochloric acid gas was bubbled through 100 ml of absolute ethanol until the increase in weight of the ethanol was approximately 5 g. Terephthalic acid, 16.6 g (0.1 mol), was then added to the acidified ethanol and the mixture heated at reflux for 31 hours. The reaction mixture was cooled, then filtered and the residue washed with ethanol. The filtrate was concentrated in-vacuo and then poured into a mixture of water and 100 ml ether. After extraction, the ether layer was separated and washed successively with water and saturated NaHCO$_3$ solution and then dried (MgSO$_4$). The ether solution was filtered and the solvent removed in-vacuo to give the title compound as a white solid. PMR (CDCl$_3$): δ 1.42 (6H, t, J~7.0 Hz), 4.40 (4H, q, J~7.0 Hz), 8.10 (4H, s).

EXAMPLE 22

Ethyl hydrogenterephthalate

Anhydrous barium hydroxide (3.83 g, 0.022 mol), was placed in a Soxhlet extractor and continuously extracted for 10 hours with hot ethanol into a refluxing mixture of 10 g (0.045 mol) of diethyl terephthalate in 100 ml of absolute ethanol. The resultant white precipitate was filtered and then washed with ethanol. The precipitate was suspended in 100 ml ether and treated with excess dilute HCl. After extraction, the ether layer was separated and washed successively with water and saturated NaCl solution and then dried (MgSO$_4$). The ether solution was filtered and the solvent removed in-vacuo. The resultant residue was recrystallized from acetonitrile to give the title compound as a white solid. PMR (CDCl$_3$): δ 1.40 (3H, t, J~7.0 Hz), 4.40 (2H, q, J~7.0 Hz), 8.10 (4H, s), 9.1 (1H, broad s).

EXAMPLE 23

Dibenzyl terephthalate

A mixture of 48.5 (0.25 mol) of dimethylterephthalate, 108 g (1.0 mol) of benzyl alcohol and 0.5 g of potssium tert-butoxide was prepared in 500 ml, 3-necked round bottom flask fitted with a magnetic stir bar, a thermometer, a nitrogen inlet and an air condenser. The stirred mixture was heated at 140° C. for 15 hours while a rapid stream of nitrogen was passed over the surface of the mixture. Most of the excess benzyl alcohol was then removed from the mixture by fractional distillation. The residue was dissolved in a mixture of ether and methylene chloride and silica was then added to the solution. The solution was then filtered and the solvent removed in-vacuo. The residual crude product was recrystallized from a mixture of hexanes and tert-butyl methyl ether to give the title compound as colorless crystals. PMR (CDCl$_3$): δ 5.38 (4H, s), 7.35–7.50 (10H, m), 8.13 (4H, s).

EXAMPLE 24

Benzyl hydrogenterephthalate

To a heated mixture of 9.1 g (26 mmol) of dibenzyl terephthalate in 90 ml acetone and 30 ml water was added dropwise a solution of 1.05 g (25 mmol) of lithium hydroxide monohydrate in 10 ml of water and 10 ml of acetone. The reaction mixture was heated at reflux for a further 30 minutes with vigorous stirring. The reaction mixture was allowed to cool and the aqueous solution was extracted with 2×10 ml of ether. The aqueous layer was then acidified with glacial acetic acid and the resultant white precipitate extracted with 3×25 ml of ether. The ether extracts were combined, washed successively with water and saturated NaCl solution and then dried (MgSO$_4$). The ether solution was then filtered and the solvent removed in-vacuo. The resultant residue was recrystallized from a mixture of acetone and water to give the captioned material as colorless crystals. PMR (CDCl$_3$): δ 5.40 (2H, s), 7.36–7.49 (5H, m), 8.18 (4H, s).

EXAMPLE 25

Ethyl (5,5,8,8-tetramethyl-5,6,7,8-tetrahydro-2-naphthyl)-terephthalate

A solution of 598.8 mg (2.9308 mmol) 5,5,8,8-tetramethyl-5,6,7,8-tetrahydro-2-naphthol, 542 mg (2.7912 mmol) of ethyl hydrogenterephthalate, 608 mg (2.9515 mmol) of 1,3-dicyclohexylcarbodiimide and 127 mg (1.0395 mmol) of 4-dimethylaminopyridine in 30 ml of methylene chloride was stirred at room temperature for 22 h. The reaction mixture was filtered and the residue washed with 10 ml of methylene chloride. The filtrate was concentrated in-vacuo and the resultant crude product purified by flash chromatography (silica; 6% ethyl acetate in hexanes) giving the captioned material as a white solid. PMR (CDCl$_3$): δ 1.32 (6H, s), 1.33 (6H, s), 1.46 (3H, t, J~7.2 Hz), 1.73 (4H, s), 4.46 (2H, q, J~7.2 Hz), 7.02 (1H, dd, J~8.5 Hz, 2.5 Hz), 7.14 (1H, d, J~2.5 Hz), 7.38 (1H, d, J~8.5 Hz), 8.19 (2H, d, J~8.1 Hz), 8.29 (2H, d, J~8.1 Hz).

Using the same general procedure, but using benzyl hydrogenterephthalate instead, benzyl (5,5,8,8-tetramethyl-5,6,7,8-tetrahydro-2-naphthyl)-terephthallate was synthesized as a white solid. PMR (CDCl$_3$): δ 1.32 (6H, s), 1.33 (6H, s), 1.74 (4H, s), 5.44 (2H, s), 7.03 (1H, dd, J~8.7 Hz, 2.4 Hz), 7.16 (1H, d, J~2.4 Hz), 7.37-7.54 (6H, m), 8.23 (2H, d, J~8.7 Hz), 8.30 (2H, d, J~8.7 Hz).

EXAMPLE 26

(5,5,8,8-tetramethyl-5,6,7,8-tetrahydro-2-naphthyl)hydrogenterephthalate

A mixture of 400 mg (0.9 mmol) of benzyl (5,5,8,8-tetramethyl-5,6,7,8-tetrahydro-2-naphthyl)terephthalate, 60 mg of 10% palladium on carbon and 5 ml of ethyl acetate was stirred under a hydrogen atmosphere at room temperature for 3 hours. The reaction mixture was filtered and the filtrate evaporated to dryness in-vacuo to give the title compound as a white solid. PMR (CDCl$_3$): δ 1.30 (12H, s), 1.71 (4H, s), 7.05 (1H, dd, J~9.0 Hz, 2.7 Hz), 7.12 (1H, d, J~2.7 Hz), 7.36 (1H, d, J~9.0 Hz), 8.25 (2H, d, J~8.4 Hz), 8.31 (2H, d, J~8.4 Hz).

EXAMPLE 27

Preferably, these compounds will be administered topically using various formulations. Two formulation are given as examples here.

| Ingredient | Weight/Percent |
|---|---|
| Solution | |
| Retinoid | 0.1 |
| BHT | 0.1 |
| Alcohol USP | 58.0 |
| Polyethylene Glycol 400 NF | 41.8 |
| Gel | |
| Retinoid | 0.1 |
| BHT | 0.1 |
| Alcohol USP | 97.8 |
| Hydroxypropyl Cellulose | 2.0 |

What is claimed is:

1. A compound of the formula

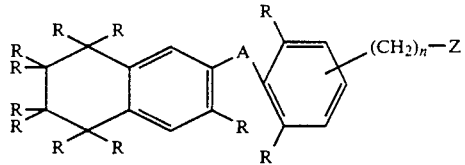

where the R groups are independently hydrogen, or lower alkyl; A is OC(O)—, —C(O)S—, or —SC(O)—; n is 0–5; and Z is —COB where B is —OH or a pharmaceutically acceptable salt, or B is —OR$_1$ where R$_1$ is an ester-forming group, or B is —N(R)$_2$ where R is independently hydrogen or lower alkyl, or Z is OE where E is hydrogen or COR$_2$ where R$_2$ is hydrogen, lower alkyl, phenyl or lower alkyl phenyl, or Z is —CHO or an acetal derivative thereof, or Z is COR$_3$ where R$_3$ is —(CH$_2$)$_m$CH$_3$ where m is 0–4 and the sum of n and m does not exceed 4.

2. A compound of claim 1 where A is —O(CO)—; n is 0–2; the position-3 group is lower alkyl; z is COB where B is OH or B is —OR$_1$ where R$_1$ is a lower alkyl group or B is —N(R)$_2$ or a pharmaceutically acceptable salt thereof, or Z is OE where E is hydrogen or COR$_2$ where R$_2$ is hydrogen, lower alkyl, phenyl or lower alkyl phenyl, or Z is CHO or an acetal derivative thereof.

3. A compound of claim 1 where A is —OC(O)—; n is 0–2; Z is COB where B is OH or B is —OR$_1$ where R$_1$ is a lower alkyl group or B is —N(R)$_2$ or a pharmaceutically acceptable salt thereof, or Z is OE where E is hydrogen or COR$_2$ where R$_2$ is hydrogen, lower alkyl, phenyl or lower alkyl phenyl, or Z is CHO or an acetal derivative thereof.

4. A method for treating psoriasis in a mammal which method comprised administering alone or in conjunction with a pharmaceutically acceptable excipient, a therapeutically effective amount of a compound according to claim 1.

5. A pharmaceutical composition comprising a pharmaceutically acceptable excipient and a therapeutically effective amount compound of the formula according to claim 1.

6. A compound of which is ethyl 4-(5,5,8,8-tetramethyl-5,6,7,8-tetrahydro-2-naphthyl)terephthalate.

7. A compound which is (5,5,8,8-tetramethyl-5,6,7,8-tetrahydro-2-naphthyl)hydrogenterephthalate.

8. The compound which is benzyl (5,5,8,8-tetramethyl-5,6,7,8-tetrahydro-2-naphthyl)terephtallate.

9. A compound of the formula

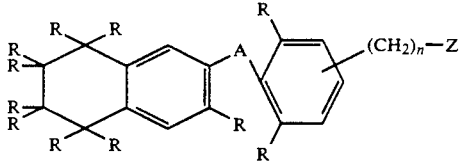

where the R groups are independently hydrogen, or lower alkyl; A is OC(O)— or —SC(O)—; n is 0–5; and Z is H, —COB where B is —OH or a pharmaceutically acceptable salt, or B is —OR$_1$ where R$_1$ is an ester-forming group, or B is —N(R)$_2$ where R is independently hydrogen or lower alkyl, or Z is OE where E is hydrogen or an ether-forming group or COR$_2$ where R$_2$ is hydrogen, lower alkyl, phenyl or lower alkyl phenyl, or Z is —CHO or an acetal derivative thereof, or Z is COR$_3$ where R$_3$ is —(CH$_2$)$_m$CH$_3$ where m is 0–4 and the sum of n and m does not exceed 4.

10. A compound of claim 9 where A is —SC(O)—.

11. A compound of claim 9 where A is —OC(O)—.

* * * * *

UNITED STATES PATENT AND TRADEMARK OFFICE
CERTIFICATE OF CORRECTION

PATENT NO. : 5,231,113

DATED : July 27, 1993

INVENTOR(S) : roshantha A. S. Chandraratna

It is certified that error appears in the above-identified patent and that said Letters Patent is hereby corrected as shown below:

Column 1, line 61, "sum" should be —sun—;

Column 15, line 28, "d)," should be —s),—;

Column 17, line 56, "3,4,5,8,8" should be —3,5,5,8,8—;

Column 20, line 27, after "1.75-1.84" insert — (2H, m), 2.81 —;

Column 24, line 20, before "group" add —R—;

Column 11, line 66, "iodide.-" should be —iodide/—.

Signed and Sealed this

Twenty-sixth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,231,113
DATED : July 27, 1993
INVENTOR(S) : Roshantha A. S. Chandraratna It is certified that error appears in the above-identified patent and that said Letters Patent is hereby corrected as shown below:

Column 3, line 22, "sufficeintly" should be —sufficiently—;

Column 3, line 24, "a" should be —as—;

Column 3, line 55, "4-methoxymethyl)phenyl)" should be —(4-methoxymethyl)phenyl—;

Column 3, line 57, "4-tert-butyldimethylsiloxymethy ) 1phenyl" should be —(4-tert-. butyldimethylsiloxymethyl)phenyl—;

Column 3, line 59, "4-formylphenyl)" should be —(4-formyl)phenyl—;

Column 3, line 61, before "4-" add —(—;

Column 14, line 37, "Hz))" should abe —Hz)—;

Column 16, line 59, "4-tetrahydronaphthtalene" should be —4-tetrahydronaphthalene—;

Column 17, line 15, "hours" should be —hour—;

column 22, line 32, "potssium" should be --potassium--.

Column 23, line 51, "formulation" (2nd occurrence) should be--formulations--.

Signed and Sealed this

Twentieth Day of September, 1994

Attest:

BRUCE LEHMAN

Attesting Officer          Commissioner of Patents and Trademarks